United States Patent
Li

(10) Patent No.: US 9,398,865 B2
(45) Date of Patent: *Jul. 26, 2016

(54) ENDOBRONCHIAL TUBE APPARATUS

(71) Applicant: Medtronic Xomed, Inc., Jacksonville, FL (US)

(72) Inventor: Wenjeng Li, Saint Johns, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/747,257

(22) Filed: Jun. 23, 2015

(65) Prior Publication Data

US 2015/0282732 A1    Oct. 8, 2015

Related U.S. Application Data

(63) Continuation of application No. 13/688,818, filed on Nov. 29, 2012, now Pat. No. 9,060,744.

(51) Int. Cl.
| | |
|---|---|
| *A61B 5/0492* | (2006.01) |
| *A61B 5/00* | (2006.01) |
| *A61M 16/04* | (2006.01) |
| *A61B 5/0488* | (2006.01) |
| *A61M 16/08* | (2006.01) |

(52) U.S. Cl.
CPC ........... *A61B 5/0492* (2013.01); *A61B 5/04886* (2013.01); *A61B 5/6847* (2013.01); *A61B 5/6853* (2013.01); *A61M 16/0404* (2014.02); *A61M 16/0434* (2013.01); *A61M 16/0833* (2014.02); *A61M 16/0443* (2014.02); *A61M 16/0459* (2014.02); *A61M 2230/60* (2013.01)

(58) Field of Classification Search
CPC ............. A61B 5/0492; A61B 5/04886; A61B 5/6853; A61B 5/687
See application file for complete search history.

(56) References Cited

U.S. PATENT DOCUMENTS

| | | | |
|---|---|---|---|
| 5,125,406 A | 6/1992 | Goldstone et al. | |
| 5,379,765 A | 1/1995 | Kajiwara et al. | |
| 6,443,156 B1 | 9/2002 | Niklason et al. | |
| 9,060,744 B2 * | 6/2015 | Li ........................ | A61B 5/6853 |
| 2011/0071379 A1 | 3/2011 | Rea et al. | |
| 2011/0245647 A1 | 10/2011 | Stanislaus et al. | |
| 2012/0024292 A1 | 2/2012 | Sandmore et al. | |

FOREIGN PATENT DOCUMENTS

| | | |
|---|---|---|
| DE | 19750705 C1 | 3/2000 |
| WO | 2011041690 A1 | 4/2011 |
| WO | 2013008106 A1 | 1/2013 |

OTHER PUBLICATIONS

PCT Search Report for PCT/US2013/072193, mailed Mar. 11, 2014, 18 pgs.

* cited by examiner

*Primary Examiner* — Lee S Cohen

(74) *Attorney, Agent, or Firm* — Dicke, Billig & Czaja, PLLC

(57) ABSTRACT

Concepts presented herein include an apparatus for monitoring EMG signals of a patient's laryngeal muscles. The apparatus includes an endobronchial tube having an exterior surface and two lumens for providing ventilation. Conductive ink electrodes are formed on the exterior surface of the endobronchial tube. The conductive ink electrodes are configured to receive the EMG signals from the laryngeal muscles when the endotracheal tube is placed in a trachea of the patient. At least one conductor is coupled to the conductive ink electrodes and is configured to carry the EMG signals received by the conductive ink electrodes to a processing apparatus.

18 Claims, 3 Drawing Sheets

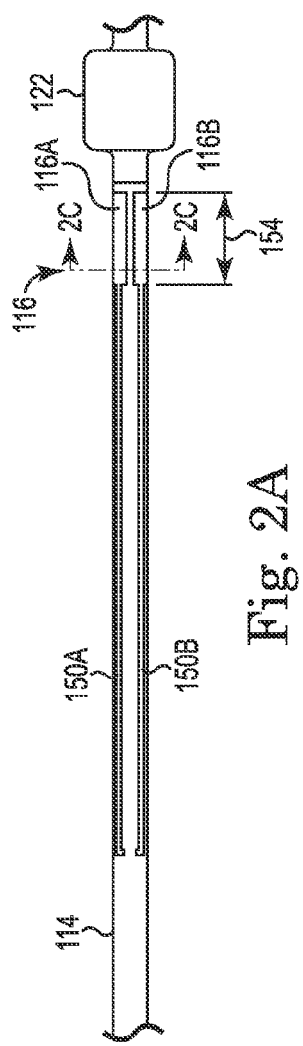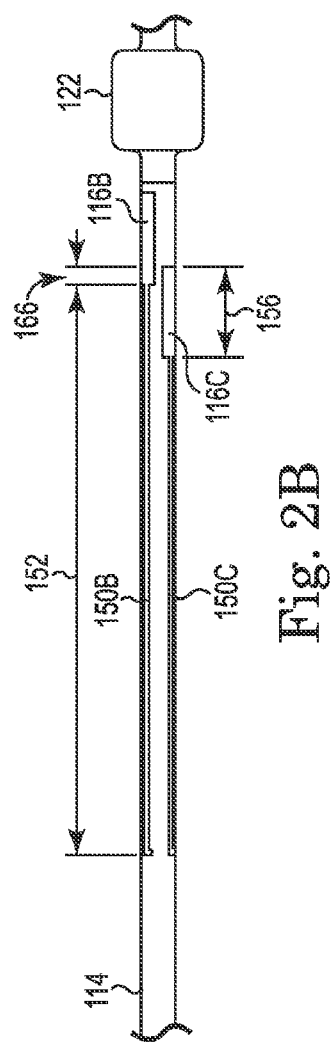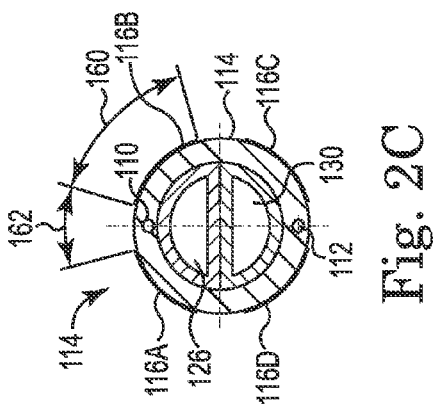

a
ENDOBRONCHIAL TUBE APPARATUS

CROSS-REFERENCE TO RELATED APPLICATIONS

This application is a continuation of U.S. application Ser. No. 13/688,818, filed Nov. 29, 2012, now U.S. Pat. No. 9,060,744, the specification of which is incorporated by reference herein.

BACKGROUND

Endobronchial tubes (also known as dual-lumen endotracheal tubes) provide an open airway for patient ventilation during surgery. In particular, endobronchial tubes are used during surgical procedures to provide ventilation to individual lungs separately. Current endobronchial tubes include a first, tracheal lumen and a second, bronchial lumen. Each lumen includes an associated inflatable cuff, the cuff associated with the tracheal lumen being positioned within the trachea and the cuff associated with the bronchial lumen being positioned within one of the bronchus.

SUMMARY

Concepts presented herein include an apparatus for monitoring EMG signals of a patient's laryngeal muscles. The apparatus includes an endobronchial tube having an exterior surface and two lumens for providing ventilation. Conductive ink electrodes are formed on the exterior surface of the endobronchial tube. The conductive ink electrodes are configured to receive the EMG signals from the laryngeal muscles when the endotracheal tube is placed in a trachea of the patient. At least one conductor is coupled to the conductive ink electrodes and is configured to carry the EMG signals received by the conductive ink electrodes to a processing apparatus.

BRIEF DESCRIPTION OF THE DRAWINGS

FIGS. 2A and 2B are different side views of an endobronchial tube.

FIG. 2C is a sectional view of the endobronchial tube illustrated in FIG. 2A.

DETAILED DESCRIPTION

Figure 1:
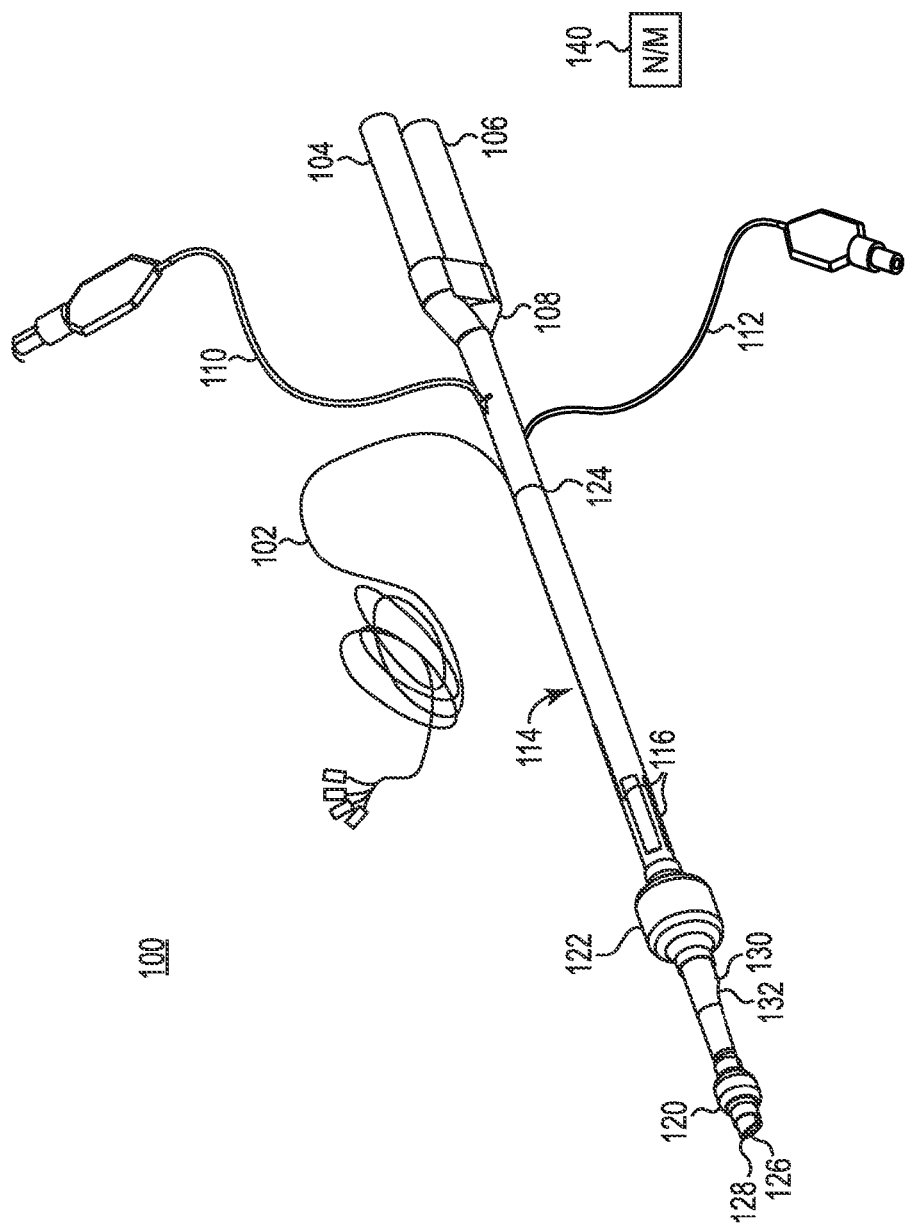
FIG. 1 is a schematic view of an EMG endobronchial tube.

FIG. 1 shows an EMG endobronchial tube 100 made from extruded polymer. Endobronchial tube 100 includes solid wires 102, a bronchial fitting 104, a tracheal fitting 106, a y-connector 108, a bronchial cuff inflating conduit 110, a tracheal cuff inflating conduit 112, extruded polymer tube 114, electrodes 116, bronchial cuff 120 and tracheal cuff 122. Solid wires 102 are connected to electrodes 116 at an interconnection 124. Tube 114 transports gases to and from the lungs. In particular, tube 114 defines a first, bronchial lumen 126 extending from bronchial fitting 104 to an opening 128 distal the bronchial cuff 120 and a second, tracheal lumen 130 extending from tracheal fitting 106 to an opening 132 distal the tracheal cuff 122. The Y-connector 108 fluidly couples the bronchial fitting 104 and tracheal fitting 106 to bronchial lumen 126 and tracheal lumen 130, respectively.

Fittings 104 and 106 are configured to be connected to a respirating machine (not shown) for injecting air into the lungs and withdrawing air from the lungs. Cuff inflating conduits 110 and 112 are configured to be connected to a source of compressed air (not shown) for inflating cuffs 120 and 122. Cuff inflating conduit 110 communicates with a lumen located in the wall of tube 114, and the lumen communicates with bronchial cuff 120. Likewise, tracheal cuff inflating conduit 112 communicates within a lumen located in the wall of tube 114, and the lumen communicates with tracheal cuff 122. During use, one of the fittings (e.g., bronchial fitting 104) is configured to inject air into one lung while the other fitting (e.g., tracheal fitting 106) is configured to injected air into the other lung. For example, cuff 120 can be positioned into the left bronchus and cuff 122 positioned into the trachea. In this case, opening 126 is positioned to direct air into the left lung from bronchial fitting 104 while opening 132 is positioned to direct air into the right lung from tracheal fitting 106. Selectively, air can be provided to only one of the fittings 104, 106 so as to provide air to only a single lung and collapsing the other lung. In such a case, a surgeon can operate proximate the collapsed lung or on the collapsed lung. After endobronchial tube 100 is inserted into the trachea of a patient, electrodes 116 sense EMG signals, which are output to an EMG processing machine, such as nerve integrity monitor (NIM) device 140, via solid wires 102. Die cut tape may be used to tape tube 114 to a patient's mouth to secure the tube and keep it appropriately positioned.

In one embodiment, the NIM 140 is configured to determine when the electrodes 116 are in contact with the vocal folds, and is configured to provide an alert to the surgeon when such contact is lost. In one embodiment, the NIM 140 is also configured to determine whether the electrodes 116 are in contact with muscle or tissue based on the received signals In one embodiment, tube 114 is a braided tube that is more flexible than conventional solid polymer tubes, and that reduces kinking. Tube 114 according to one embodiment is formed from a braided polymer or nitinol within a thin-walled tube, and reduces or eliminates rotation of the tube at the vocal folds, while allowing a proximal portion of the tube to rotate.

FIG. 2A shows a first side view (posterior side) of endobronchial tube 114 with four electrodes 116. FIG. 2B shows a second side view (rotated 90 degrees from the view shown in FIG. 2A) of the endobronchial tube 114 shown in FIG. 2A. FIG. 2C is a diagram illustrating a cross-sectional view of the endobronchial tube 114 shown in FIGS. 2A and 2B.

Electrodes 116 include four electrodes 116A-116D, which are formed around a circumference of the tube 114 and extend in a longitudinal direction of the tube 114. Electrodes 116A and 116B are positioned entirely on the posterior side of the tube 114 and are also referred to herein as posterior electrodes 116A and 116B. Electrodes 116C and 116D are positioned entirely on the anterior side of the tube 114 and are also referred to as anterior electrodes 116C and 116D. The anterior side of the tube 114 is the bottom half of the tube 114 shown in FIG. 2C, and the posterior side of the tube 114 is the top half of the tube 114 shown in FIG. 2C. Each of the electrodes 116A-116D is coupled to a respective trace 150A-150D (trace 150D is not visible in the Figures). Traces 150A-150D are positioned in a protected (masked) region 152 of tube 114. Posterior electrodes 116A and 116B are positioned in an exposed (unmasked) region 154 of tube 114. Anterior electrodes 116C and 116D are positioned in an exposed (unmasked) region 156 of tube 114.

In one embodiment, each of the electrodes 116A-116D has a length of about one inch, and extends laterally around a circumference of the tube for a distance corresponding to an angle 160 of about 60 degrees (i.e., each of the electrodes 116A-116D has a width of about 16.67 percent of the total circumference of the tube). The electrodes are laterally spaced apart around the circumference of the tube by a distance corresponding to an angle 160 of about 30 degrees (i.e., the lateral spacing between each of the electrodes 116A-116D is about 8.333 percent of the total circumference of the tube). The posterior electrodes 116A and 116B are longitudinally offset or displaced from the anterior electrodes 116C and 116D. The posterior electrodes 116A and 116B are positioned closer to the distal end (right side in FIGS. 2A and 2B) of the tube 114 than the anterior electrodes 116C and 116D, and the anterior electrodes 116C and 116D are positioned closer to the proximal end (left side in FIGS. 2A and 2B) of the tube 114 than the posterior electrodes 116A and 116B.

Tube 114 includes an overlap region 166 where a proximal portion of the posterior electrodes 116A and 116B longitudinally overlap with a distal portion of the anterior electrodes 116C and 116D. The electrodes 116 do not physically overlap each other since they are laterally offset from each other. In one embodiment, the overlap region 166 is about 0.1 inches long, and the overall length from a proximal end of the anterior electrodes 116C and 116D to a distal end of the posterior electrodes 116A and 116B is about 1.9 inches. In another embodiment, the overlap region 166 is about 0.2 inches long, and the overall length from a proximal end of the anterior electrodes 116C and 116D to a distal end of the posterior electrodes 116A and 116B is about 1.8 inches. Tube 114 is configured to be positioned such that the vocal folds of a patient are positioned in the overlap region 166. Thus, the configuration of the electrodes 116 above the vocal folds is different than the configuration below the vocal folds. The posterior electrodes 116A and 116B are configured to be positioned primarily below the vocal folds, and the anterior electrodes 116C and 116D are configured to be positioned primarily above the vocal folds. In one embodiment, electrodes 116A and 116C are used for a first EMG channel, and electrodes 116B and 116D are used for a second EMG channel.

In an alternate embodiment, all four surface printed electrodes, 116A, 116B, 116C and 116D, are equal in length. This will allow the finish product to be placed with little concerns of rotational alignment.

As illustrated in FIG. 2C, conduits 110 and 112 are formed in a thickness of the tube 114 to carry compressed air to bronchial cuff 120 and tracheal cuff 122, respectively. Additionally, inside tube 114 are formed bronchial lumen 126 and tracheal lumen 130. During use, one of the lumens 126 and 130 can be used to inject gases into a particular lung while the other lumen is sealed from injecting gases into the opposite lung.

Figure 3:
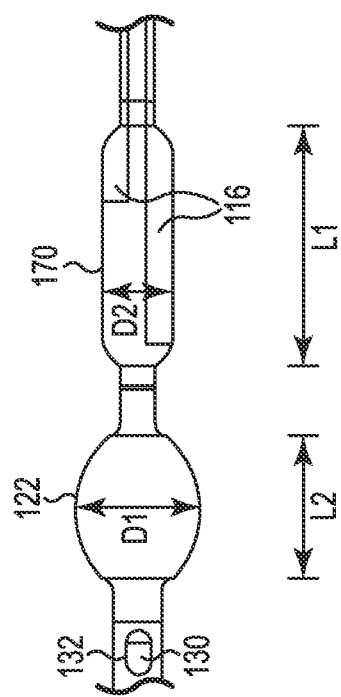
FIG. 3 is a partial side view of an endobronchial tube having an electrode cuff.

With reference to FIG. 3, another embodiment includes an electrode cuff 170 positioned proximal the tracheal cuff 122. In the embodiment of FIG. 3, cuff 122 is of a different shape than that illustrated in FIGS. 1-2C. Other shapes for the cuffs 122 and 170 can be utilized. Electrodes 116 are applied directly to the electrode cuff 170 and are similar to that discussed above. Cuffs 122 and 170 are sized so as to both provide suitable sealing between the trachea and cuff 122 yet provide suitable compliance of electrode cuff 170 in contact with the vocal folds of a patient when inflated by pressurized fluid provided within inflating conduit 110. Upon inflation, the tracheal cuff 122 has a larger diameter D1 than a diameter D2 of electrode cuff 170. In some embodiments, the diameter D2 is selected to be approximately half the diameter D1. In one example, D1 is about 20 millimeters, whereas D2 is about 9 millimeters. In yet a further embodiment, D1 is approximately 27 millimeters, whereas D2 is approximately 14 millimeters. Moreover, a length L1 of the cuff 170 is selected to be greater than a length L2 for cuff 122. In one embodiment, the L1 is approximately 1.875 inches. In another embodiment, L1 is in a range from approximately 1.5 inches to 2.5 inches. In a further embodiment, a ratio of D1:L1 is selected to be in a range from approximately 15:100 to 30:100.

Furthermore, a compliance for cuff 170 is selected so as to prevent trauma due to cuff 170 contacting the vocal folds of the patient. In one embodiment, the cuff 170 is formed of a semi-compliant balloon. The semi-compliant balloon will increase in diameter about 10 to 20 percent from a nominal pressure to a rated burst pressure for the balloon. In a further embodiment, cuff 170 is formed of a compliant balloon such that the balloon will increase in diameter from 20 to 200 percent from a nominal pressure to a rated burst pressure of the balloon. In a further embodiment, the cuff 170 is formed of a compliant material that has a greater compliance than a material selected for cuff 122. In one embodiment, cuff 122 has a compliance defined as increasing in diameter about 20 to 200 percent from a nominal pressure to a rated burst pressure for the cuff 122.

Inflating conduit 110 extends along the length of tube 114 to electrode cuff 170 and continues in extension to the tracheal cuff 122. Due to relative compliance of the cuffs 122 and 170, cuff 122 is configured to fluidly seal the trachea of a patient when positioned, whereas electrode cuff 170 inflates to contact the vocal folds of the patient so as to prevent trauma from occurring due to contact between the cuff 170 and the vocal folds. Furthermore, by selecting diameters D1 and D2 of cuffs 122 and 170, tension exerted on an exterior surface of each cuff is adjusted. In one embodiment, thickness and diameter for cuffs 122 and 170 are selected such that cuff 122 will absorb pressure and reduce pressure on cuff 170. In this configuration, cuff 170 can conform to a shape of vocal folds and ensure sufficient electrical contact between the electrodes 112 and the vocal folds without causing irritation by exerting too much pressure on the vocal folds.

Although the present disclosure has been described with reference to preferred embodiments, workers skilled in the art will recognize that changes can be made in form and detail without departing from the spirit and scope of the present disclosure.

What is claimed is:

1. An apparatus for monitoring electromyographic signals of a patient's laryngeal muscles, comprising:
   an endobronchial tube defining first and second lumens;
   a first cuff coupled to the endobronchial tube and positioned proximate a first opening fluidly coupled with the first lumen, the first cuff sized to be positioned within a bronchus of the patient;
   a second cuff coupled to the endobronchial tube and positioned proximate a second opening fluidly coupled with the second lumen, the second cuff configured to be positioned within a trachea of the patient;
   an electrode cuff coupled to the endobronchial tube and positioned proximal to the first cuff and the second cuff; and
   electrodes positioned on an exterior surface of the electrode cuff.

2. The apparatus of claim 1, wherein the electrodes include four electrodes positioned around a circumference of the exterior surface.

3. The apparatus of claim 1, further comprising a Y-connector coupled to the endobronchial tube, the Y-connector fluidly coupling first and second fittings to the first and second lumens, respectively.

4. The apparatus of claim 1, further comprising an interconnection coupled to the tube and conductive traces electrically connecting the electrodes with the interconnection.

5. The apparatus of claim 1, further comprising first and second inflating conduits fluidly coupled to the first and second cuffs, respectively.

6. The apparatus of claim 5, wherein the electrode cuff is fluidly coupled to the second inflating conduit.

7. The apparatus of claim 1, wherein the second cuff is formed of a first material exhibiting a first compliance and wherein the electrode cuff is formed of a second material exhibiting a second compliance, greater than the first compliance.

8. The apparatus of claim 1, wherein the electrodes are conductive ink electrodes.

9. The apparatus of claim 1, wherein the electrodes are positioned such that, when the first cuff is positioned within the bronchus and the second cuff is positioned within the trachea, the electrodes are in contact with vocal folds of the patient.

10. A method for monitoring electromyographic signals of a patient's laryngeal muscles, comprising:
    providing an endobronchial tube defining first and second lumens, the endobronchial tube including electrodes positioned on an exterior surface of an electrode cuff of the endobronchial tube;
    positioning a bronchial cuff within a bronchus of the patient, the bronchial cuff being coupled to the endobronchial tube;
    positioning a tracheal cuff within a trachea of the patient, the tracheal cuff coupled to the endobronchial tube, wherein the electrode cuff is positioned proximal to the bronchial cuff and the tracheal cuff; and
    measuring signals of the patient using the electrodes.

11. The method of claim 10, wherein the electrodes include four electrodes positioned around a circumference of the exterior surface.

12. The method of claim 10, further comprising:
    coupling a Y connector to the endobronchial tube, the Y connector fluidly coupling first and second fittings to the first and second lumens, respectively.

13. The method of claim 10, further comprising electrically connecting the electrodes to an interconnection on the endobronchial tube with conductive traces.

14. The method of claim 10, further comprising:
    inflating the bronchial and tracheal cuffs using first and second inflating conduits, respectively.

15. The method of claim 14, further comprising:
    inflating the electrode cuff using the second inflating conduit.

16. The method of claim 10, wherein the tracheal cuff is formed of a first material exhibiting a first compliance and wherein the electrode cuff is formed of a second material exhibiting a second compliance, greater than the first compliance.

17. The method of claim 10, wherein the electrodes are conductive ink electrodes.

18. The method of claim 10, further comprising:
    positioning the electrodes in contact with vocal folds of the patient.

* * * * *